Jan. 21, 1936. M. GERBER Plant Pat. 164

CHERRY VARIETY

Filed Feb. 8, 1934

Inventor:
Menno Gerber
By Hiram B. Swartz Atty.

Patented Jan. 21, 1936

Plant Pat. 164

UNITED STATES PATENT OFFICE

164

CHERRY VARIETY

Menno Gerber, Orrville, Ohio

Application February 8, 1934, Serial No. 710,281

1 Claim. (Cl. 47—62)

My invention relates to improvements in cherries, and particularly to a late ripening variety of sweet cherry, and comprehends my discovery of a seedling cherry tree and its fruit of unknown ancestry or parentage. The tree is now apparently about twenty years old, and grew in a somewhat neglected spot on a farm in Wayne County, Ohio, about latitude 40° north, and was fortuitously discovered by me in the spring of 1933. and has since then been asexually propagated by grafting into young trees which are now thriftily growing in the same locality.

The tree now grown to full proportions is about twenty feet high and fifteen feet wide, and has a single trunk, about twelve inches thick near its base. The tree and its fruit tend to show Mazzard parentage, and under comparable orchard conditions in this vicinity its general appearance and characteristics resemble other sweet cherry trees, except the following four particulars—First, this tree grown in the same neighborhood with many other cherry trees of the common early ripening fruit, rivals them all in vitality and abundant fruitage and leafage, and does not ripen until near two months later, viz—from August first to August fifteenth, after all other cherries are gone.

Second, it blooms several days earlier than any other well known varieties, and third, the fruit hangs much longer on the tree after it ripens without decay or rot, as during the last season sound cherries were gathered from the tree as late as September first. A fourth characteristic is the fact that the fruit is so solid and firm that it will not easily crush, and will not bleed when the stem is withdrawn, so that the cherries may be gathered and stored without loss of rotundity or bleeding, or spoiling occasioned thereby.

The foregoing characteristics clearly distinguish this cherry from all other known varieties. Its unusually late ripening makes it very valuable from the canner's viewpoint as well as from that of the home orchard and its persistence in hanging on the tree so long after ripening thereon, without loss or decay, adds value to its variety, by its avoidance of glut on the market; and its sustained perfection when not promptly picked after it has ripened, prevents loss in handling and shipping.

Figure 1:
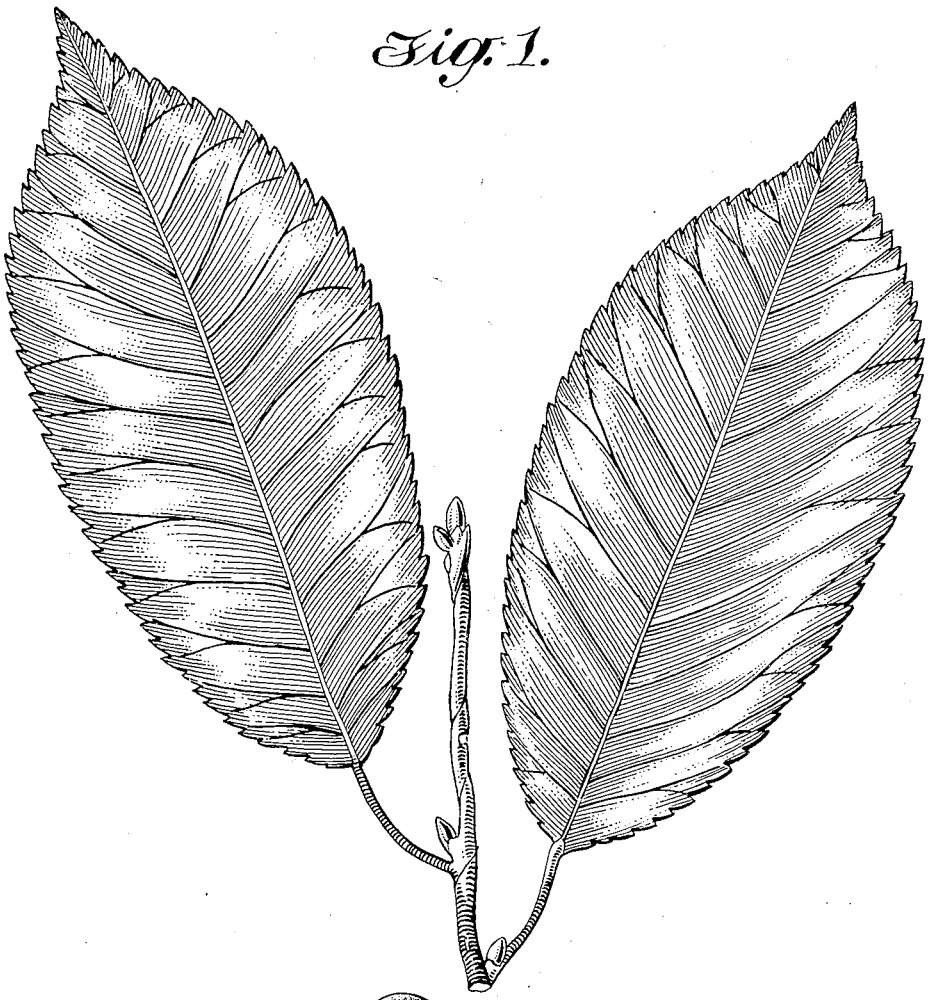
Figure 2:
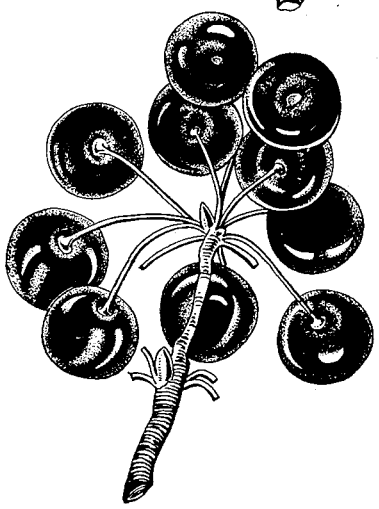

The drawing shows—in Fig. 1, the natural configuration of its leaves; and Fig. 2 shows substantially the rotundity of its fruit, and thriftiness, thereof, which are very unusual and attractive features for the market.

The following is a more technical description of this tree and its fruit, covering foliage, flower, and fruit:

*First observed in 1933.*—Maturity very late, ripening between one and two months after other standard varieties have been gathered. Size—¾ inch in length and width, practically rotund or roundish. Base slightly broader than apex—stem slender 1¼″ to 1½ inches long; cavity narrow and shallow; suture generally merely a line; color deep purplish when fully ripe, turning to almost black if not picked when ripe; skin tough; flesh very firm; juice darker than flesh and skin;—juice does not escape when stem is pulled out of cherry. Hangs long on tree after ripe if not picked. Quality very good, sweet, luscious. Stone small, clingish, smooth and longish; ⅜ inch long, ¼ inch thick, and $\frac{3}{16}$ inch wide.

Another observer reports: Its fruit matures very late (description prepared August 1, 1934) normal ripening date for the variety which is August 1–15; 13/16 inch diameter (length and width equal), cordate, compressed; cavity intermediate in depth and width, flaring, suture indistinct; apex pointed slightly, somewhat rounded; color purplish red; dots numerous, small, obscure; stem 1¼–1½ inches long, adherent to the fruit; skin thin, separating readily from the pulp; flesh purplish red, lighter than the skin, juice darker than flesh, meaty, pleasant flavored, mild, sweet; of very good dessert quality;—stone practically free, ovate, slightly flattened and oblique, with smooth surfaces, 6–16 inch x 8/16 inch. Fruit occurs singly, doubly, and in clusters from spurs.

A third observer reports: On the first day of August 1934, I had the privilege of testing fruit from the August ripening cherry tree owned by Menno Gerber, of near Orrville, Ohio.

This fruit could be described as of medium size, ¾″ in diameter, slightly oblong to almost round. cavity of medium depth; stem 1¼ inches long. Apex rounded. Skin of medium thickness. Flesh dark red, tender, meaty, sweet. Juice dark red. Stone flat and semi-free.

When the stem was removed from the fruit the juice did not exude as is true of many sweet cherries. This character should be a factor in the keeping quality of the fruit. On the date examined, August 1, 1934, the fruit was approaching maturity. The picking date for this year would range from August 1 to 10th. It should be stated that because of unseasonable dry weather the picking dates for fruits of all kinds has been somewhat earlier, perhaps a week or ten days earlier than the average year. This would make the picking date at least 4 weeks later than such standard varieties of sweet cherries as Lambert, Bing, Schmidt, Napoleon, Yellow Spanish and Windsor, as grown in the Experiment Station orchards some 15 miles west of the location of the tree from which the samples described were taken.

*Leaves.*—Oblong, pointed, doubly serrate, large.

*Flower.*—Similar to other cherries, but blooms a few days earlier than any other.

I claim:

The cherry tree and fruit as described, said tree ripening its fruit from August first to fifteenth, and having the characteristics stated.

MENNO GERBER.